United States Patent [19]

de Reinach Hirtzbach et al.

[11] 4,383,849
[45] May 17, 1983

[54] 2,3-DIHYDRO-4-PYRONE DERIVATIVES, THEIR PREPARATION THE HERBICIDAL COMPOSITIONS IN WHICH THEY ARE PRESENT AND THEIR USE FOR SELECTIVELY DESTROYING WEEDS IN CROPS

[75] Inventors: Francois de Reinach Hirtzbach; Guy Borrod, both of Lyons, France

[73] Assignee: Rhone-Poulenc Agrochimie, Lyons, France

[21] Appl. No.: 315,981

[22] Filed: Oct. 28, 1981

[30] Foreign Application Priority Data

Nov. 14, 1980 [FR] France ................. 80 24698

[51] Int. Cl.³ .................. A01N 43/16; C07D 309/22
[52] U.S. Cl. ........................................ 71/88; 549/420
[58] Field of Search .............. 260/345.8 R; 71/88; 549/420

[56] References Cited

U.S. PATENT DOCUMENTS 4,060,533 11/1977 Nadelson ............... 260/345.7 R
4,297,367 10/1981 Guigues et al. ........ 260/345.8 R
4,316,737 2/1982 Guigues et al. ........ 260/345.8 R

OTHER PUBLICATIONS

Gelin et al., Bull. Soc. Chim. Fr., (1), 288–298 (1968).

Primary Examiner—Nicky Chan
Attorney, Agent, or Firm—Scully, Scott, Murphy & Presser

[57] ABSTRACT

The invention relates to new 2,3-dihydro-4-pyrone derivatives.

These compounds correspond to the formula:

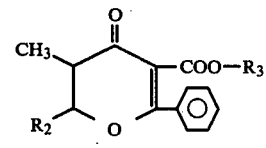

in which $R_2$ represents an alkyl radical ($C_2$–$C_3$) and $R_3$ represents and alkyl radical ($C_1$–$C_4$), an alkenyl radical ($C_3$–$C_5$) or an alkynyl radical ($C_3$–$C_5$).

They can be used for destroying weeds in crops, in particular sunflower and cotton crops.

6 Claims, No Drawings

2,3-DIHYDRO-4-PYRONE DERIVATIVES, THEIR PREPARATION THE HERBICIDAL COMPOSITIONS IN WHICH THEY ARE PRESENT AND THEIR USE FOR SELECTIVELY DESTROYING WEEDS IN CROPS

The invention relates to new 2,3-dihydro-3-methyl-6-phenyl-4-pyrone derivatives, their preparation, the compositions, for agricultural use, in which they are present and their use for selectively destroying weeds in crops, in particular sunflower and cotton crops.

French patent application No. 2,419,940 describes, as herbicides, 2,3-dihydro-6-phenyl-4-pyrone derivatives substituted on the phenyl nucleus and corresponding to the formula (I):

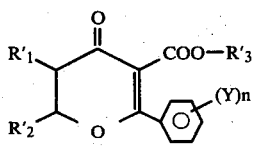

in which: $R'_1$ and $R'_2$ can represent a hydrogen atom or an alkyl radical containing from 1 to 4 carbon atoms, or can together form an alkylene chain containing from 2 to 6 carbon atoms, $R'_3$ can represent, amongst other meanings, an alkyl radical containing from 1 to 4 carbon atoms, an alkenyl radical containing from 2 to 4 carbon atoms or an alkynyl radical containing from 2 to 4 carbon atoms, Y represents a halogen atom, an alkyl radical containing from 1 to 4 carbon atoms or an alkoxy radical containing from 1 to 4 carbon atoms and n is an integer equal to 1 or 2. According to this French Patent Application No. 2,419,940, the index n cannot have the value zero and hence the herbicidal compounds described by this patent application are necessarily substituted on the phenyl radical.

This French patent application No. 2,419,940 indicates, on pages 2 and 14, that the preferred compounds are those in which the 6-phenyl radical comprises, as a substituent, a fluorine atom in the 4-position on the said phenyl radical.

Finally, in the remark which it makes concerning the reference Bull. Soc. Chem. de France 1968n, No. 1, pages 288–298, this French patent application indicates that the 2,3-dihydro-5-carbethoxy-6-phenyl-4-pyrones unsubstituted on the phenyl and described in this reference exhibit virtually no herbicidal activity.

This French patent application in fact teaches that, in the case of 2,3-dihydro-2,3-dialkyl-6-phenyl-4-pyrone derivatives, the obtainment of good herbicidal properties depends on the presence of a suitable substituent on the phenyl radical, and that, in the absence of any substituent on this phenyl radical, the obtainment of satisfactory herbicidal properties must not be expected.

It has now been found that, unexpectedly in view of the teachings of this French patent application, certain new 2,3-dihydro-6-phenyl-4-pyrone derivatives unsubstituted on the phenyl exhibit an excellent herbicidal activity, which enables them to be used as herbicides for destroying weeds in crops, at very low doses per hectare.

One object of the present invention is to propose 2,3-dihydro-6-phenyl-4-pyrone derivatives unsubstituted on the phenyl nucleus and hence more convenient and more economical to manufacture.

Another object of the present invention is to propose 2,3-dihydro-6-phenyl-4-pyrone derivatives unsubstituted on the phenyl nucleus but nevertheless, and surprisingly, exhibiting an excellent herbicidal activity towards a large number of both graminaceous and dicotyledon weeds.

Another object of the present invention is to propose 2,3-dihydro-6-phenyl-4-pyrone derivatives unsubstituted on the phenyl radical and exhibiting an excellent tolerance towards important crops, such as, in particular, sunflower and cotton, so as to enable them to be used for destroying weeds in the said crops.

It has now been found that these objects can be achieved by virtue of the new 2,3-dihydro-3-methyl-6-phenyl-4-pyrone derivatives which form the subject of the present patent application.

These new derivatives correspond to the formula:

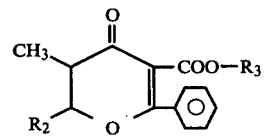

in which: $R_2$ represents an ethyl radical, a n-propyl radical or an isopropyl radical and $R_3$ represents an alkyl radical containing from 1 to 4 carbon atoms, an alkenyl radical containing from 3 to 5 carbon atoms or an alkynyl radical containing from 3 to 5 carbon atoms.

Each of the compounds according to the formula (II) can exist in two disastereoisomeric forms of different polarities, one of which has the cis configuration and the other the trans configuration. In the text of the present application, it will be considered that the less polar isomer is the isomer having the trans configuration and that the more polar isomer is the isomer having the cis configuration.

For greater convenience, these isomers will hereinafter be designated respectively by "trans isomer" and "cis isomer".

The work carried out by the Applicant Company has shown that, in the case of the compounds according to the formula (II), the cis isomers generally exhibit a very much greater herbicidal activity than the corresponding trans isomers.

Thus, the invention relates more particularly to the compounds according to the formula (II) wherein each of these compounds is for the major part in the form of the cis isomer (i.e. wherein more than 50% by weight is in the form of the cis isomer).

The invention preferably relates to the compounds according to the formula (II) essentially consisting of the cis isomer.

The expression "essentially consisting of the cis isomer" is understood in the present description to mean that the percentage by weight of cis isomer in the compound in question is greater than or equal to 90% and less than or equal to 100%.

Amongst the compounds corresponding to the formula (II), the invention preferably relates to the compounds, for the major part in the form of the cis isomer, in which $R_2$ represents the ethyl radical and $R_3$ has the same meaning as in the formula (II), but preferably represents an alkyl radical containing from 1 to 3 carbon atoms or the propargyl radical.

Amongst these preferred compounds, the invention relates more particularly to 2,3-dihydro-2-ethyl-3-methyl-5-ethoxycarbonyl-6-phenyl-4-pyrone, the said compound essentially consisting of the cis isomer (90 to 100% by weight of cis isomer). Preferably the invention relates to the cis isomer of this compound.

The experiments carried out by the Applicant Company have in fact shown that this cis isomer surprisingly exhibits a quite remarkable level of herbicidal activity, which is substantially greater than that of the other compounds claimed by the present patent application.

The compounds according to the invention which correspond to the formula (II) can be prepared in accordance with a method analogous to that described in the abovementioned French patent application and comprising the following steps:

Step A

Reaction of a benzoylacetic acid derivative with a magnesium alcoholate, optionally prepared in situ, according to the equation:

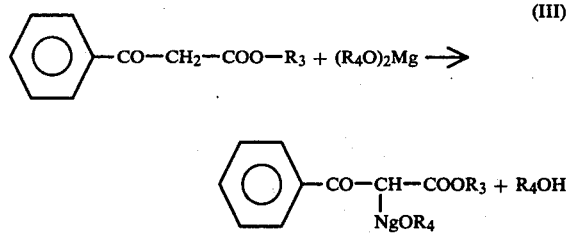

(III)

in which $R_3$ has the same meaning as in the formula (II) and $R_4$ represents an alkyl radical containing from 1 to 4 carbon atoms.

The reaction is carried out in an anhydrous inert organic medium, such as e.g. benzene, toluene or ethyl ether, by keeping the temperature at between about 0° and 100° C. during the addition of the reactants, and then, when this addition has ended, by heating the reaction medium at a temperature between about 35° and 150° C. until the reaction has ended.

As the magnesium alcoholate, it is preferred to use magnesium ethylate, which can be prepared in situ by reacting magnesium with ethanol, in an anhydrous inert organic medium, in the presence of carbon tetrachloride.

Step B

Reaction of the chloride of an ethylenic acid with the alkoxymagnesium derivative (III) resulting from the preceding step, to give the compound (IV) in equilibrium with its enol form (V), according to the equation:

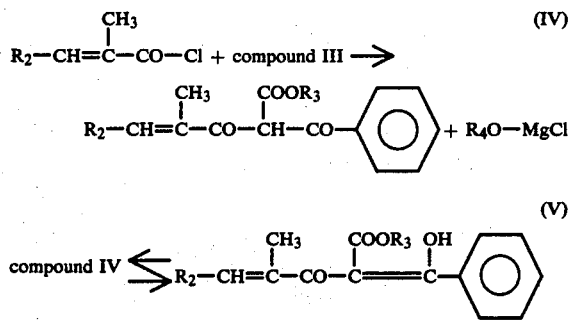

in which $R_2$ and $R_3$ have the same meaning as in the formula II and $R_4$ has the same meaning as in step A.

The reaction is carried out in an anhydrous inert organic medium, such as ethyl ether, toluene or benzene, at a temperature between about 0° and 20° C. Under these conditions, the equilibrium between the compound (IV) and its enol form (V) is strongly displaced in the direction of the formation of the latter compound.

Step C

Cyclisation of the compound (V) resulting from the preceding step, to give the compound (II), according to the equation:

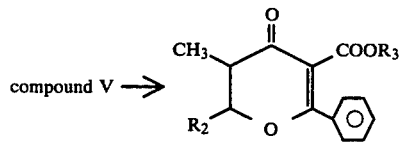

in which $R_2$ and $R_3$ have the same meaning as in the formula (II), and decomposition, by hydrolysis, of the compound of the formula $R_4O$—MgCl resulting from the preceding step.

This reaction is carried out by initially treating the reaction mixture comprising the compound (V) and the compound of the formula $R_4O$—MgCl by means of a dilute aqueous solution of a strong acid, such as sulphuric acid, at a temperature between 0° and 20° C., which sometimes causes partial cyclisation of the compound (V) and the decomposition of the compound of the formula $R_4O$—MgCl by hydrolysis, and by subsequently treating the partially cyclised compound (V), separated off beforehand, with a dilute anhydrous alcoholic solution of a strong acid, such as hydrochloric acid, at a temperature between about 60° and 100° C., the said acid optionally being prepared in situ. For the latter treatment, the purpose of which is to complete the cyclisation of the compound (V), it is preferred to use a dilute anhydrous ethanolic solution of hydrochloric acid, prepared in situ by reacting a small amount of acetyl chloride with ethanol.

When the cyclisation is complete, the compound (II) can be isolated by any known means, such as e.g. by filtration, distillation of the solvent, recrystallisation of the products formed in the reaction medium, and so on. If necessary, it can be purified by customary methods, such as recrystallisation, molecular distillation, liquid phase chromatography, and so on.

The compound (II) thus obtained generally consists of a mixture of the cis isomer and the trans isomer, the latter generally being formed as the major component.

The cis isomer of the compound of the formula (II) can be separated from the mixture of isomers resulting from step C of the process described above, by liquid phase chromatography under pressure, a methylcyclohexane/ethyl acetate mixture advantageously being used as the eluting mixture.

The following examples are described in order to illustrate the invention without however limiting it.

The structure of the compounds obtained was confirmed by nuclear magnetic resonance spectrometry (NMR), the spectra having been run at 60 megahertz as continuous-wave spectra, in deuterochloroform, with tetramethylsilane as the internal standard.

EXAMPLE 1

Preparation of 2,3-dihydro-2-ethyl-3-methyl-5-carbethoxy-6-phenyl-4-pyrone (compound No. 1) of the formula:

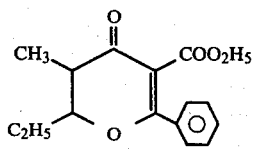

Ethyl benzoylacetate (23.04 g; 0.12 mol), anhydrous toluene (400 ml) and magnesium ethylate (13.68 g; 0.12 mol) are introduced into a three-necked round-bottomed flask fitted with a central mechanical stirrer, a thermometer, a dropping funnel and a Vigreux column surrounded by a distillation head.

The reaction medium is heated gradually until the toluene-ethanol azeotrope distils. The temperature inside the reactor gradually rises to 112° C. This temperature is maintained for 60 minutes, the distilled liquid being replaced by anhydrous toluene.

After cooling to 5° C., a solution of 2-methylpent-2-enoyl chloride (17.9 g; 0.135 mol) in toluene (70 ml) is added in the course of 20 minutes. When the addition has ended, the temperature is raised to 35° C. and the medium is stirred for 60 minutes at 35° C.

The medium is then cooled to 10° C. and hydrolysed by 2 N sulphuric acid (250 ml).

The organic phase is decanted. The aqueous phase is extracted with toluene (50 ml). The organic phases are combined and washed with water until the washings are neutral. After drying over sodium sulphate and evaporation of the toluene, the oil obtained is taken up in absolute ethanol (300 ml) and acetyl chloride (2 ml). This solution is heated under reflux for 60 minutes. After cooling and concentration, the oil obtained is taken up in a methylcyclohexane/ethyl acetate mixture (7/3) (200 ml). By crystallisation, a white product (17.4 g, i.e. 50% of theory) is thus obtained.

This product was analysed by thin layer chromatography on a Merck silica plate eluted with a toluene-/ethyl acetate mixture (8/2).

An examination of this plate under ultra-violet light with a wavelength equal to 254 nanometers (nm) shows the presence of two spots of which the frontal ratios (Rf) are 0.5 and 0.4 and correspond respectively to the trans isomer and the cis isomer.

These two isomers were separated by liquid phase chromatography under pressure, in a methylcyclohexane/ethyl acetate eluant mixture (7/3). The following are thus obtained:

The less polar isomer referred to as the trans isomer (12.18 g), melting at 97°-98° C. The chemical shift of the hydrogen in the 2-position on the pryone ring equals 4.2.

The more polar isomer referred to as the cis isomer (5.22 g), melting at 101°-102° C. The chemical shift of the hydrogen in the 2-position on the pyrone ring equals 4.55.

The ethyl benzoylacetate used as the starting material is a commercially available product.

The 2-methylpent-2-enoyl chloride was obtained by reacting thionyl chloride with 2-methylpent-2-enoic acid in accordance with a method which is in itself known.

EXAMPLE 2

By following the method described in Example 1, using the appropriate starting materials, the compounds below were prepared in the form of their cis and trans isomers:

Compound No. 2:

2,3-dihydro-2-ethyl-3-methyl-5-propargyloxycarbonyl-6-phenyl-4-pyrone:
the less polar isomer (trans): m.p. 90.8° C.,
the more polar isomer (cis): m.p. 74.5°-75° C.

Compound No. 3:

2,3-dihydro-2-ethyl-3-methyl-5-methoxycarbonyl-6-phenyl-4-pyrone:
the less polar isomer (trans): m.p. 127.5° C.
the more polar isomer (cis): m.p. 96.0° C.

Compound No. 4:

2,3-dihydro-2-n-propyl-3-methyl-5-ethoxycarbonyl-6-phenyl-4-pyrone:
the less polar isomer (trans): m.p. 62.1° C.
the more polar isomer (cis): m.p. 78.6° C.

Compound No. 5:

2,3-dihydro-2-ethyl-3-methyl-5-n-propoxycarbonyl-6-phenyl-4-pyrone:
the less polar isomer (trans): m.p. 80.6° C.
the more polar isomer (cis): m.p. 76.5° C.

Compound No. 6:

2,3-dihydro-2-ethyl-3-methyl-5-allyloxycarbonyl-6-phenyl-4-pyrone:
the less polar isomer (trans): m.p. 57.5° C.
the more polar isomer (cis): m.p. 65.5° C.

EXAMPLE I herbicidal activity, in a greenhouse, in the
pre-emergence treatment of plant species.

A number of seeds are sown in $9 \times 9 \times 9$ cm pots filled with light agricultural earth, this number being determined as a function of the plant species and the size of the seed.

The seeds are then covered with an approximately 3 mm thick layer of earth.

After moistening the earth, the pots are treated by spraying each pot with an amount of spraying mixture which corresponds to a volume of 500 liters/hectare and contains the active ingredient at the relevant dose.

The spraying mixture was prepared by diluting a wettable powder having the following composition by weight:

| | |
|---|---|
| active ingredient to be tested | 20% |
| solid inert carrier: kaolinite | 69% |
| surface-active agent (deflocculant): calcium lignosulphonate | 5% |
| surface-active agent (wetting agent): sodium alkylarysulphonate | 1% |
| anti-caking silica | 5% | with an amount of water determined so as to obtain the desired concentration.

This powder was obtained by mixing and grinding the ingredients in a microniser so as to obtain an average particle size of less than 40 microns.

According to the concentration of active ingredient in the spraying mixture, the dose of active ingredient applied with 0.5 kg/hectare, 1 kg/hectare and 4 kg/hectare.

The treated pots are then placed in troughs which are intended to receive the moistening water, by sub-irrigation, and are kept for 35 days at ambient temperature under 70% relative humidity.

After 35 days, the number of living plants in the pots treated with the spraying mixture containing the active ingredient to be tested, and the number of living plants in a control pot treated under the same conditions, but with a spraying mixture which does not contain active ingredient, are evaluated. The percentage destruction of the treated plants, relative to the untreated control, is thus determined. A percentage destruction equal to 100% indicates that there has been complete destruction of the plant species in question, and a percentage of 0% indicates that the number of living plants in the treated pot is identical to that in the control pot.

The experiment was carried out on various plant species, both adventitious plants and crops, using the cis isomer of 2,3-dihydro-2-ethyl-3-methyl-5-carbethoxy-6-phenyl-4-pyrone, described in Example 1, as the active ingredient. The observed values of percentage destruction are indicated in the table below:

| Dose of active ingredient | 0.5 kg/ hectare | 1 kg/ hectare | 4 kg/ hectare |
|---|---|---|---|
| Adventitious plants | | | |
| Wild oat (Avena fatua) | 10 | 90 | |
| Finger grass (Digitaria sanguinalis) | 100 | 100 | |
| Panic grass (Echinochloa crus-galli) | 100 | 100 | |
| Ray grass (Lolium multiflorum) | 40 | 100 | |
| Foxtail grass (Setaria faberii) | 100 | 100 | |
| Slender foxtail (Alopecurus myosuroides) | 95 | 100 | |
| Goosefoot (Chenopodium sp) | 100 | 100 | |
| Black night-shade (Solanum nigrum) | 100 | 100 | |
| Mustard (Sinapis arvensis) | 100 | 100 | |
| Chickweed (Stellaria media) | 50 | 95 | |
| Crops | | | |
| Cotton (Gossypium barbadense) | 0 | 0 | 0 |
| Sunflower (Helianthus annus) | 0 | 0 | 0 |
| Soft wheat (Triticum vulgare) | 0 | 0 | 50 |
| Maize (Zea mays) | 0 | 5 | 80 |

These results show the excellent herbicidal activity of this compound, even at very low doses of active ingredient, on the majority of the adventitious plants treated, namely both graminaceous and dicotyledon plants, and also its selectivity towards the crops in question and very particularly towards cotton and sunflower.

EXAMPLE II herbicidal activity, in a greenhouse, of the cis isomers of compounds Nos. 1, 2, 3 and 4 in the pre-emergence treatment of plant species.

The method described in Example I is followed, but the wettable powder is replaced by emulsifiable concentrate comprising the following by weight:

| | |
|---|---|
| active ingredient | 20% |
| 14:1 ethylene oxide/nonylphenol condensate (surface-active agent) | 7% |
| calcium dodecylbenzenesulphonate (surface-active agent) | 3% |
| xylene (solvent) | 70% |

The observed values of percentage destruction, expressed as in Example I, are indicated in the table below, in which the plant species tested are represented by the following abbreviations:

| | Abbreviation |
|---|---|
| Adventitious plants | |
| Wild oat (Avena fatua) | AVE |
| Finger grass (Digitaria sanguinalis) | DIG |
| Panic grass (Echinochloa crus-galli) | ECH |
| Ray grass (Lolium multiflorum) | LOL |
| Foxtail grass (Setaria faberii) | SET |
| Slender foxtail (Alopecurus myosuroides) | ALO |
| Goosefoot (Chenopodium sp) | CHE |
| Black night-shade (Solanum nigrum) | SOL |
| Mustard (Sinapis arvensis) | SIN |
| Chickweed (Stellaria media) | STE |
| Crops | |
| Cotton (Gossypium barbadense) | GOS |
| Sunflower (Helianthus annus) | HEL |

By way of comparison, the results obtained under the same conditions for α,α,α-trifluoro-2,6-dinitro-N,N-dipropyl-p-toluidine, which is a herbicide known by the common name of trifluralin, have been indicated in the first column of this table.

| | | COMPOUND TESTED | | | | | | | |
|---|---|---|---|---|---|---|---|---|---|
| | | No.1 cis isomer | | No.2 cis isomer | | No.3 cis isomer | | No.4 cis isomer | |
| Dose kg/ hectare | Comparison 0.5 | 0.5 | 2 | 0.5 | 2 | 0.5 | 2 | 0.5 | 2 |
| Adventitious plants | | | | | | | | | |
| AVE | 0 | 10 | 100 | 0 | 85 | 0 | 5 | 0 | 30 |
| DIG | 100 | 100 | 100 | 100 | 100 | 80 | 100 | 100 | 100 |
| ECH | 100 | 100 | 100 | 40 | 100 | 5 | 90 | 50 | 80 |
| LOL | 90 | 100 | 100 | 5 | 100 | 0 | 50 | 100 | 100 |
| SET | 100 | 100 | 100 | 80 | 100 | 60 | 100 | 100 | 100 |
| ALO | 100 | 100 | 100 | 95 | 100 | 20 | 100 | 95 | 100 |
| CHE | 50 | 100 | 100 | 100 | 100 | 60 | 100 | 50 | 100 |
| SOL | 0 | 100 | 100 | 90 | 100 | 60 | 100 | 100 | 100 |
| SIN | 0 | 100 | 100 | 20 | 95 | 0 | 80 | 20 | 90 |
| STE | 20 | 70 | 100 | 90 | 100 | 20 | 100 | 30 | 85 |
| Crops | | | | | | | | | |
| HEL | 0 | 0 | 0 | 0 | 0 | 0 | 0 | 0 | 0 |

| Dose kg/ hectare | Comparison | COMPOUND TESTED | | | | | | | |
|---|---|---|---|---|---|---|---|---|---|
| | | No.1 cis isomer | | No.2 cis isomer | | No.3 cis isomer | | No.4 cis isomer | |
| | 0.5 | 0.5 | 2 | 0.5 | 2 | 0.5 | 2 | 0.5 | 2 |
| GOS | 0 | 0 | — | 0 | — | 0 | 0 | 0 | — |

These results show the excellent herbicidal activity of the compounds according to the invention, even at very low doses of active ingredient, on the majority of the adventitious plants treated, namely both graminaceous and dicotyledon plants, and also their selectivity towards cotton and sunflower.

For their use in practice, the compounds according to the invention are rarely employed by themselves, but most frequently in the form of compositions which also form part of the invention and which generally contain, in addition to the active ingredient according to the invention, one or more solid or liquid carriers acceptable in agriculture and/or one or more surface-active agents, also acceptable in agriculture.

In the present account, the term "carrier" denotes an organic or inorganic, natural or synthetic material with which the active ingredient is combined in order to facilitate its application to the plants or to the soil. The carrier can be solid (clays, natural or synthetic silicates, silica, resins, waxes, solid fertilisers or the like) or liquid (water, alcohols, petroleum fractions, aromatic or paraffinic hydrocarbons, chlorohydrocarbons, liquefied gases or the like).

The surface-active agent can be an emulsifying, dispersing, deflocculating or wetting agent of ionic or non-ionic type. The examples which may be mentioned are salts of polyacrylic acids, salts of lignosulphonic acids, salts of phenolsulphonic or naphthalenesulphonic acids, condensates of ethylene oxide with fatty alcohols, fatty acids or fatty amines, substituted phenols (in particular alkylphenols or arylphenols), salts of sulphosuccinic acid esters, taurine derivatives (in particular alkyltaurates), and phosphoric acid esters of condensates of ethylene oxide with alcohols or with phenols.

In general, the compositions according to the invention usually contain from about 0.01 to 95% (by weight) of one or more compounds according to the invention, one or more solid or liquid carriers and/or one or more surface-active agents.

However, these compositions can also contain all kinds of other ingredients, such as e.g. thickeners, thixotropic agents, protective colloids, adhesives, penetrating agents, stabilisers and the like, and also other known active ingredients having pesticidal properties (in particular herbicidal, fungicidal and insecticidal properties), properties which assist plant growth (in particular fertilisers) or properties which regulate plant growth. More generally, the compounds according to the invention can be combined with all the solid or liquid additives corresponding to the customary techniques for the preparation of pesticidal compositions.

The compositions according to the invention can be prepared in the form of wettable powders, dusting powders, granules, solutions, emulsifiable concentrates, emulsions, suspension concentrates and aerosols.

The wettable powders, or spraying powders, usually contain from 20 to 95% by weight of active ingredient and generally contain, in addition to a solid carrier, from 0 to 5% by weight of wetting agent and from 3 to 10% by weight of one or more stabilisers and/or other additives, such as penetrating agents, adhesives or anti-caking agents, dyestuffs and the like.

They are prepared by mixing the constituents in mixers and by grinding them in mills or other suitable grinders, e.g. air grinders, so as to obtain the desired particle size.

The composition of a 50% strength wettable powder is given below by way of example (percentages by weight):

| | |
|---|---|
| active ingredient (cis isomer of the compound described in Example No.1) | 50% |
| sodium isopropylnaphthalenesulphonate (anionic wetting agent) | 1% |
| sodium lignosulphonate (deflocculant) | 5% |
| anti-caking silica | 5% |
| kaolin | 39% |

Another example of a wettable powder is given below:

| | |
|---|---|
| active ingredient (cis isomer of the compound described in Example 1) | 50% |
| sodium alkylarylsulphonate | 2% |
| low-viscosity methylcellulose | 2% |
| diatomaceous earth | 46% |

The granules, which are intended to be placed on the soil, are usually prepared so that they have dimensions of between 0.1 and 2 mm, and they can be manufactured by agglomeration or impregnation. In general, the granules will contain from 0.5 to 25% of active ingredient and from 0 to 10% by weight of additives, such as stabilisers, slow-release modifiers, binders and solvents.

The emulsifiable concentrates, which can be applied by spraying, usually contain from 10 to 50% by weight/volume of active ingredient. In addition to the active ingredient and the solvent, they can also contain, if necessary, from 2 to 20% by weight/volume of suitable additives, such as surface-active agents, stabilisers, penetrating agents, corrosion inhibitors, dyestuffs and adhesives.

The composition of an emulsifiable concentrate containing 100 g/liter of active ingredient is given below by way of example:

| | |
|---|---|
| active ingredient (cis isomer of the compound described in Example 1) | 103 g |
| solvent (xylene) | 707 g |
| 10:1 ethylene oxide/nonylphenol condensate | 70 g |
| calcium dodecylbenzenesulphonate | 30 g |

The suspension concentrates, which can also be applied by spraying, are prepared so as to give a stable fluid product which does not form a deposit, and they usually contain from 10 to 75% by weight of active ingredient, from 0.5 to 15% by weight of surface-active agent, from 0.1 to 10% by weight of thixotropic agents, from 0 to 10% of suitable additives, such as anti-foam agents, corrosion inhibitors, stabilisers, penetrating agents and adhesives, and, as the carrier, water or an organic liquid in which the active ingredient is essentially insoluble; certain organic solids, or inorganic salts, can be dissolved in the carrier in order to assist in preventing sedimentation or to act as antifreeze agents for the water.

The aqueous dispersions and aqueous emulsions, which are obtained by diluting the abovementioned compositions with water, in particular the wettable powders and emulsifiable concentrates according to the invention, are also included in the general scope of the present invention. The emulsions thus obtained can be of the water-in-oil type or of the oil-in-water type and they can have a thick consistency such as that of a mayonnaise.

All these aqueous dispersions and aqueous emulsions, or spraying mixtures, can be applied to the crops in which weeds are to be destroyed, by any suitable means, mainly by spraying, at doses which are generally of the order of 500 to 1,000 liters of spraying mixture per hectare.

As indicated above, the invention also relates to a process for destroying weeds in crops, such as cotton and sunflower crops, in accordance with which an effective amount of at least one of the compounds according to the invention is applied to the plants and/or to the soil in the zone in which weeds are to be destroyed. Generally, amounts of active ingredients ranging from 0.2 to 4 kg/hectare give good results, it being understood that the choice of the amount of active ingredient to be used depends on the severity of the problem to be solved, on the climatic conditions and on the crop in question. The treatment is generally carried out as a pre-emergence treatment of the crops and adventitious plants, or as a pre-sowing treatment of the crops, with incorporation into the soil, although in certain cases, depending on the compound used, good results can also be obtained by means of post-emergence treatments.

We claim:

1. A 2,3-dihydro-3-methyl-6-phenyl-4-pyrone derivative essentially consisting of the cis isomer of the general formula:

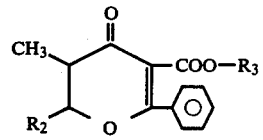

wherein $R_2$ is ethyl, and $R_3$ is an alkyl radical having from 1 to 3 carbon atoms or propargyl.

2. A compound according to claim 1 which essentially consists of the cis isomer of 2,3-dihydro-2-ethyl-3-methyl-5-ethoxycarbonyl-6-phenyl-4-pyrone.

3. A compound according to claim 2 which is the cis isomer of 2,3 dihydro-2-ethyl-3-methyl-5-ethoxycarbonyl-6-phenyl-4-pyrone.

4. A herbicidal composition for agricultural use which contains, as the active ingredient, a herbicidally effective amount of a compound according to any one of claims 1, 2 or 3.

5. A composition according to claim 4 which contains, in addition to the active ingredient a carrier and/or a surface active agent which can both be used in agriculture.

6. A process for selectively destroying weeds in sunflower and cotton crops which comprises applying to the situs of these crops a herbicidally effective amount of a compound according to any one of claims 1, 2 or 3.

* * * * *